(12) United States Patent
Caleffi

(10) Patent No.: US 6,790,346 B2
(45) Date of Patent: Sep. 14, 2004

(54) CYCLONE SEPARATOR SUITABLE FOR VARIABLE FLUID FLOW RATES

(75) Inventor: Ideo Caleffi, Sala Baganza (IT)

(73) Assignee: Cattani S.p.A., Parma (IT)

( * ) Notice: Subject to any disclaimer, the term of this patent is extended or adjusted under 35 U.S.C. 154(b) by 0 days.

(21) Appl. No.: 10/623,504

(22) Filed: Jul. 22, 2003

(65) Prior Publication Data

US 2004/0074828 A1 Apr. 22, 2004

(30) Foreign Application Priority Data

Jul. 24, 2002 (EP) ............................................ 02425482

(51) Int. Cl.⁷ ........................ A61C 17/06; B01D 21/26; B04C 5/13; B04C 5/30
(52) U.S. Cl. ........................ 210/136; 210/123; 210/194; 210/512.1; 433/92; 209/719; 209/725; 96/158; 96/168; 55/459.1
(58) Field of Search ................................ 210/123, 136, 210/194, 512.1; 433/92; 209/719, 725; 96/158, 168; 55/459.1

(56) References Cited

U.S. PATENT DOCUMENTS

| 5,108,608 A | 4/1992 | Carroll |
| 5,888,579 A | 3/1999 | Lun |

*Primary Examiner*—David A. Reifsnyder
(74) *Attorney, Agent, or Firm*—Young & Thompson

(57) ABSTRACT

Cyclone separator with flow rate regulation for separating solid particles from a fluid, comprises a recipient having a fluid inlet and an upper outlet for clarified fluid. The separator also comprises a recycling conduit which places an outlet conduit in communication with the inlet, a three-way valve to an inlet of which the outlet conduit is connected, and to outlets of which the recycling conduit and the outlet are connected. The three-way valve has an obturator which can block the connection between the outlet conduit and the recycling conduit, a one-way valve which has an obturator and is located at the outlet downstream of the three-way valve. The one-way valve is normally closed and can connect the outlet conduit with the outlet. The three-way valve and the one-way valve are brought into action when the fluid pressure in outlet from the separator reaches first and second predetermined values.

7 Claims, 2 Drawing Sheets

CYCLONE SEPARATOR SUITABLE FOR VARIABLE FLUID FLOW RATES

BACKGROUND OF THE INVENTION

Specifically, though not exclusively, the invention is usefully applied in separating solid particles discharge fluids in dental apparatus.

As is well known, dental aspiration plants remove fluids from the mouth of a patient during an operation. These fluids comprise a gaseous part (generally air), a liquid part (generally water, blood and other liquids which are used in dental apparatus) and a solid part in particle form (usually the amalgam used in fillings). The aspirated fluids contain various polluting substances, such as for example solid particles of amalgam. In dental apparatus the production of polluting fluids can be quite abundant, although generally discontinuous. These fluids, before being discharged into the sewers, must be freed of polluting substances.

The prior art teaches separating the solid particles from the fluids by means of a cyclone separator which exploits the centrifugal force developed by creating a rapid vortex in the fluid flow in which the solid particles are suspended. These cyclone separators comprise a recipient having an inlet for the fluid and an upper outlet for the fluid from which the solid particles have been removed. The separator recipient has a downwards-converging truncoconical shape, at the narrow end of which there is a discharge that can be connected to a container in which the solid particles can be collected.

These separators, of extremely simple construction, operate without any external motor and entirely by the creation of a centrifugal force impressed on the particles to be separated by the fluid movement. The particles to be separated are projected against the walls of the recipient and descend towards the bottom of the separator while the fluid rises in the secondary vortex created in the central part of the separator and exits from the top part of the separator. The degree of separation of the particles greatly depends on the fluid flow rate crossing the centrifuge. With low flow rates, these separators are not able to guarantee a sufficient level of separation of the solid particles which, especially for use in dental apparatus, must be at least 95% of the total of the particles contained in the fluid.

To obviate the above-described drawback, the prior art teaches a cyclone separator, described in EP 0 557 251, by the same applicant. In this separator, the efficiency and performance of the separation are increased thanks to the use of a centrifugal pump the blade of which, located internally of the recipient and above the truncoconical part, can rotate so as to accelerate the speed of the water independently of the flow rate, and thus performs a first separation of the particles by centrifugation. The use of a centrifuge pump, which enables the separator to function both as a centrifuge separator and as a cyclone separator, is however somewhat complicated in construction and therefore expensive.

Furthermore, to pass from "centrifuge" to "cyclone" operation, the above-described separator requires the use of a solenoid valve commanded by an electrical signal coming from outside the separator, closing or opening the outlet of the separator by a command which is independent of the operative conditions of the separator. This creates yet another constructional complication and also means that the separator is dependent on the functioning of an external device.

European patent application number EP 99830011.5, which published as EP 0 933 066 A2 and is by the same applicant, teaches another solution, which has a special conformation and arrangement of the fluid inlet and outlet holes in the separator. This separator, constructionally very simple, increases the efficiency of the separation, but cannot operate at very slow flow rates.

The main aim of the present invention is to obviate the above-mentioned drawbacks in the prior art by providing a cyclone separator which is constructionally very simple and economical and which at the same time can provide a high degree of separation, independently of the flow rate of the fluid reaching the separator.

An advantage of the device is that there is no need for an auxiliary motor or command signals from the outside of the device to operate it.

A further advantage of the device is that it can be cleaned and maintained by very simple and easy operations.

These aims and more besides are achieved by the object of the invention as it is characterised by the accompanying claims.

SUMMARY OF THE INVENTION

The cyclone separator with flow rate regulation is for separating solid particles from a fluid, especially in dental apparatus. The separator comprises a recipient having an inlet for the fluid and an upper outlet for the fluid once the solid particles have been removed therefrom. The separator also comprises a recycling conduit which places an outlet conduit in communication with the inlet, a three-way valve to an inlet of which the outlet conduit is connected, and to outlets of which the recycling conduit and the outlet are connected. The three-way valve has an obturator which can block the connection between the outlet conduit and the recycling conduit, a one-way valve which has an obturator and is located at the outlet downstream of the three-way valve. The one-way valve is normally closed and can connect the outlet conduit with the outlet. The three-way valve and the one-way valve are brought into action when the fluid pressure in outlet from the separator reaches first and second predetermined values.

BRIEF DESCRIPTION OF THE DRAWINGS

Further characteristics and advantages of the invention will better emerge from the detailed description that follows, of a preferred but non-limiting embodiment illustrated purely by way of example in the accompanying figures of the drawings, in which.

DESCRIPTION OF THE PREFERRED EMBODIMENTS

Figure 1:
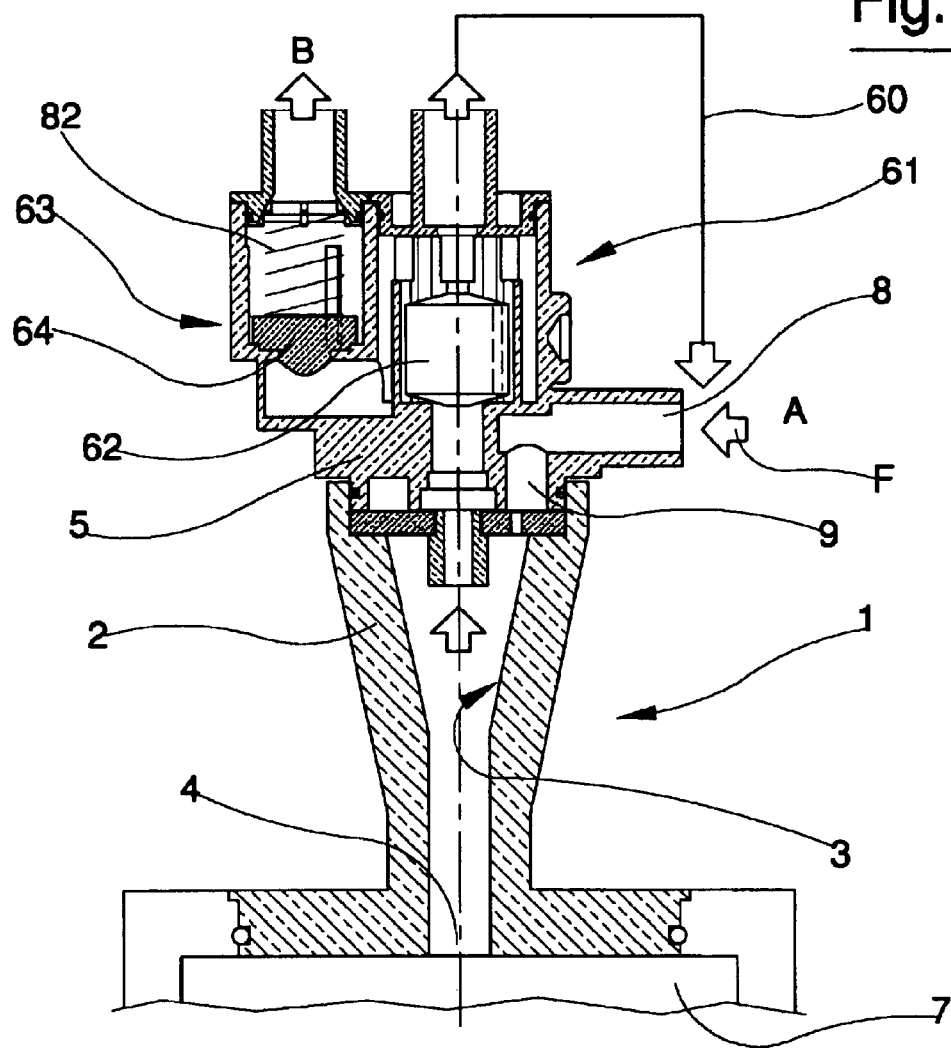
FIG. 1 is a schematic section in vertical elevation of the separator of the invention.
Figure 3:
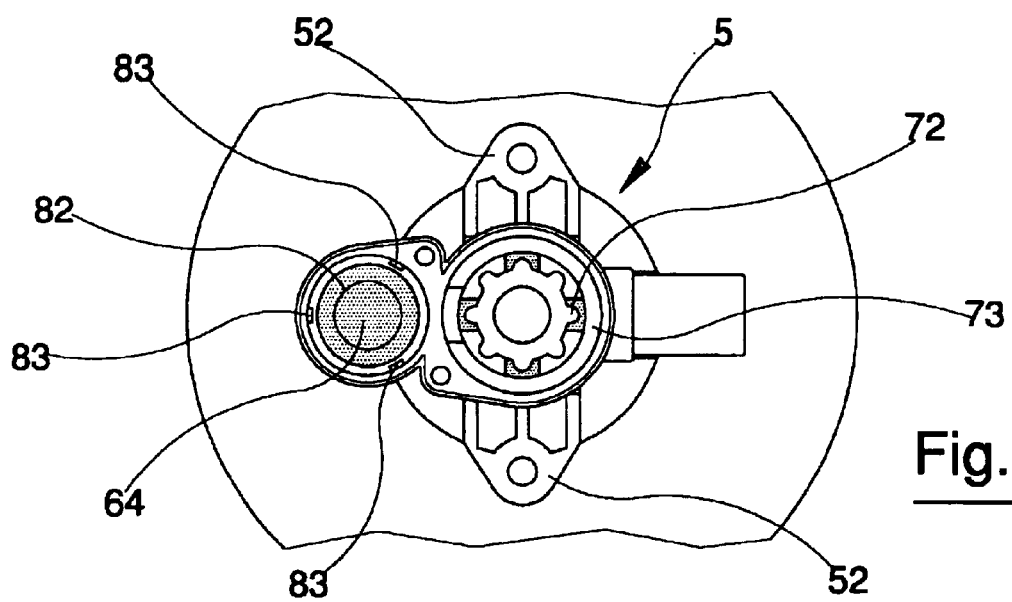
FIG. 3 is a view from above, with some parts removed better to evidence others, of the lid of the separator.
Figure 2:
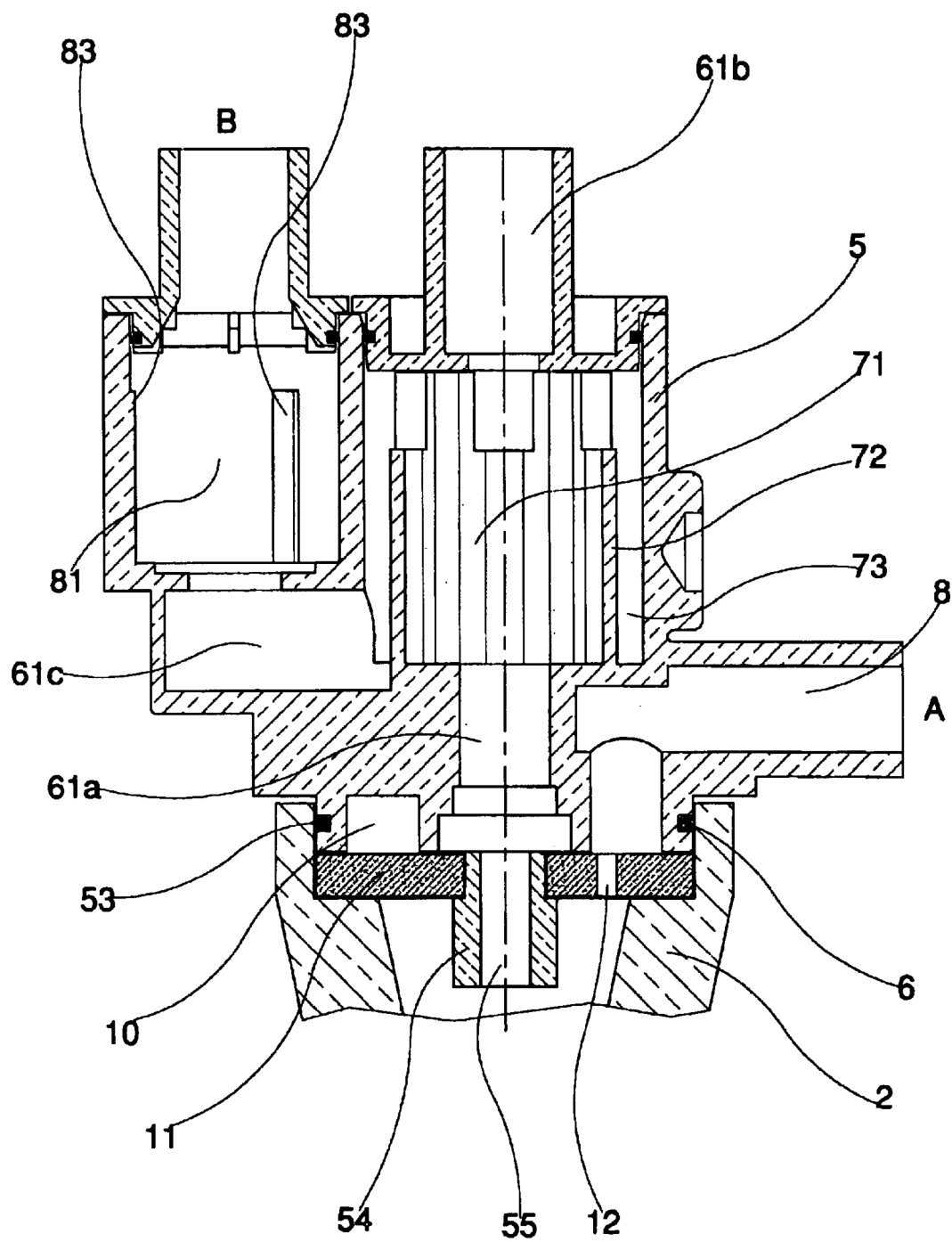
FIG. 2 is a section in vertical elevation in enlarged scale of the lid of the separator.

With reference to the figures of the drawings, 1 denotes in its entirety a cyclone separator of solid particles dispersed in a fluid which is used especially for the separation of the solid particles suspended in discharge fluids coming from dental apparatus, of known type and not illustrated. In these plants there is a production of fluids containing air, water, blood, amalgam, chemical products, etc., which must be discharged to the sewers according to anti-pollution laws which rule that certain substances, including amalgam and the like, cannot be discharged to the sewers. In the above-mentioned apparatus the production of polluting fluids is rather abundant though discontinuous. The separator of the invention has the aim of freeing the fluids of these polluting particles, independently of the flow rate of the fluid reaching the separator. The separator 1 comprises a recipient 2 which is connected to an inlet A for receiving the fluid in which the solid particles to be separated are suspended, and also comprises an upper outlet B for discharging the fluid minus the solid articles. The recipient 2, which can be made for example of a plastic material, is provided with a truncoconical wall 3 converging in a downwards direction, at the narrow neck of which a discharge 4 is located. The discharge 4 communicates with a lower collection container 7 in which the separated solid particles are accumulated.

The recipient 2 is superiorly closed by a lid 5, made for example of a plastic material, which can be coupled removably to the recipient 2, for example using fixing screws. In the preferred embodiment, the lid 5 is associated to both inlet A and outlet B.

The lid 5 laterally exhibits a first mouth 8 which affords the inlet A for receiving the fluid coming from the dental apparatus in the direction indicated by an arrow F. In this embodiment the first mouth 8 is constituted by a horizontal-axis cylindrical tube solidly connected to the lid 5.

An end of the tube, comprising the inlet A and projecting laterally from the lid. 5, is connectable to means for delivering the fluid containing the solid particles to be separated. The opposite end of the tube is united to the material of the lid 5 and communicates, through a vertical-axis conduit 9 afforded in the lid 5, with an underlying annular chamber 10 afforded in the lid 5 and not in contact with the outside. The chamber 10 is separated from the internal cavity of the recipient 2 by means of a lower wall 11 of the lid 5 which superiorly delimits the cavity.

The chamber 10 afforded in the lid 5, and therefore inlet A of the fluid, communicates with the inside of the recipient 2 through holes 12, made in the lower wall 11 of the lid 5, which preferably exhibit an oblique axis directed tangentially with respect to the vertical axis of the truncoconical wall 3.

The structure of the above-described lower wall 11 is such as to fraction the total flow of the fluid arriving via the main inlet A into a plurality of small jets which are injected tangentially in the truncoconical zone of the recipient 2. The lid 5 externally comprises a flanged lateral part 52 bearing means, of known type and not illustrated, for removably coupling with a corresponding flanged part of the underlying recipient 2, and a lower cylindrical part 53 which is for insertion (and detachment) in a corresponding cavity 2 located immediately above the truncoconical wall 3. Seals, comprising in the illustrated example an annular seal 6, are interpositioned between the cylindrical part 53 of the lid 5 and the cylindrical part of the recipient 2.

The lid 5 further exhibits a vertical-axis tubular body 54 which projects inferiorly and the internal cavity of which, which is coaxial to the truncoconical wall 3 of the recipient 2, defines an outlet conduit 55 for the fluid from the recipient 2 which outlet conduit 55 is crossed in an upwards direction by the fluid, freed of the heaviest particles, as it exits the recipient 2. The above is common to the prior art described in above-cited European patent EP 99830011.5; it is stressed, however, that the characteristics of the separator of the invention, as it will be illustrated herein below, can be applied also to a separator exhibiting a fluid inlet system (for example without the lower wall 11 or having inlet holes arranged differently) as well as a coupling system between the upper part and the recipient that are different from the ones described.

The separator of the invention comprises a recycling conduit 60 which, as will be more fully explained herein below, places the outlet conduit 55 in communication with the fluid inlet A. In the accompanying figures of the drawings the recycling conduit 60 is illustrated schematically. The recycling conduit 60 is connected upstream of the pump, not illustrated, which introduces the fluid into the separator; this is to prevent the pump from pumping fluid through the recycling conduit 60.

The lid 5 internally affords a three-way valve 61, an inlet 61a of which is connected to the outlet conduit 55, and outlets 61b and 61c of which are connected to the recycling conduit 60 and the outlet B.

The valve 61 is provided with an obturator 62 which is commanded by the pressure exerted by the fluid outletting from the outlet conduit 55. The obturator 62 intercepts the connection between the outlet conduit 55 and the recycling conduit 60 when the pressure exerted by the fluid exiting from the outlet conduit 55 reaches a first predetermined value. The inlet 61a is connected directly to the outlet conduit 55, and the outlet 61b is connected directly to the recycling conduit 60; the connection between the outlet 61c of the valve 61 and the outlet B of the fluid is achieved through a one-way valve 63, normally closed, which is located just before the outlet B and downstream of the three-way valve 61. The one-way valve 63 is provided with an obturator 64 and opens when the pressure exerted by the fluid reaches a second predetermined value which is higher than the first predetermined value.

The lid 5 affords a first chamber 71 which constitutes the body of the three-way valve 61. Internally of the first chamber 71 a calibrated float can move in an axial direction, and this constitutes the obturator 62 of the valve 61. The calibrated float is cylinder-shaped and has two truncoconical ends; it is made of metal. The float is activated directly by the fluid exiting the outlet conduit 55 and, following the action of the fluid, can assume three different positions. In a first position, the float closes the inlet 61a of the valve 61; this position is assumed due to force of gravity when there is no fluid flow from the outlet conduit 55. A second position, in which the float opens both the inlet 61a and the outlets 61b and 61c of the valve 61, is assumed when the fluid flow from the outlet conduit 55 exerts a lower pressure than the first predetermined pressure value on the float. A third position, in which the float opens both the inlet 61a and the outlet 61c of the valve 61 while closing outlet 61b thereof, which outlet 61b is connected to the recycling conduit 60, is assumed when the fluid flow coming from the outlet conduit 55 exerts an equal or superior pressure on the float to the first predetermined value.

In particular, the first chamber 71 comprises a channelled housing 72 which is directly connected to the inlet 61a and the outlet 61b of the valve 61, internally of which the obturator 62 can run, unsealed; the first chamber further comprises an annular chamber 73 which is arranged around the channelled housing 72 and is always connected both with the inside of the channelled housing 72 and with the outlet 61c of the three-way valve 61. With this arrangement the fluid, once it has entered the valve 61, can circulate freely internally of the valve at all times, independently of the position of the float. The lid 5 further comprises a second chamber 81, which constitutes the body of the one-way valve 63, which is located by a side of the first chamber 71 and is connected thereto through the outlet 61c of the three-way valve. The obturator 64 of the valve 63 can move internally of the second chamber 81; the obturator 64 normally assumes a first position, in which it closes the valve 63; this position is maintained by a calibrated elastic element 82 as long as the pressure of the fluid coming from the outlet conduit 55 and in particular the valve 61 is below the second predetermined value. The obturator 64 assumes a second position, in which the valve 63 is open, when the pressure of the fluid coming from the outlet conduit 55, and in particular from the valve 61, is equal to or above the second predetermined value.

Projecting guides 83 are located on the internal wall of the second chamber 81, which guides 83 are destined to guide the sliding of the obturator 64 without preventing passage of the fluid; once the valve 63 is open, the fluid can pass freely by the sides of the obturator 64 into the crown described between the obturator and the internal wall of the second chamber 81 thanks to the presence of the guides 83 which project internalwise of the second chamber 81.

The separator functions as described herein below.

It is important to bear in mind the fact that the separation of the solid particles is achieved by the cyclone vortices that are only created in the separator when the fluid flow rate is high; for low rates, the secondary vortex tends to draw the solid particles upwards towards the recipient 2 outlet.

The fluid enters the inlet A of the recipient 2, is subdivided into several jets which exit tangentially from the various mouths 13 and create the cyclone vortices which cause separation of the solid particles from the fluid, which solid particles are thrust outwards towards the internal walls of the recipient 2 and fall into the collection chamber 7. The fluid, devoid of the solid particles, exits from the top of the recipient 2 through the outlet conduit 55 and goes to the three-way valve 61 which, according to the fluid flow rate, i.e. the pressure exerted by the fluid exiting the outlet conduit 55, behaves in various ways. When the fluid flow is of modest entity, a condition in which solid particle separation is not of sufficient quality, the pressure that the fluid outletting from the outlet conduit 55 exerts on the obturator 62 (the calibrated float) of the valve 61 is sufficient to raise the obturator 61, thus permitting outlet of the fluid from the outlet conduit 55 towards the inside of the valve 61 body, but is not sufficient to push the valve 61 body to close the first outlet 61*b* of the valve 61. The obturator 62 is therefore in its second position (or, more precisely, in one of its possible second positions). This situation persists until the fluid flow rate reaches a level such as to exert a pressure on the obturator 62 which is equal to or above the first predetermined value; this first predetermined value is obviously determined by the weight and size of the float constituting the obturator of the valve 61.

When the above situation obtains, the fluid enters the valve 61, exits from the outlet 61*c* of the valve but cannot go further because the one-way valve 63 is closed (this valve 63 opens only when the pressure exerted by the fluid reaches the second predetermined value, which is above the first predetermined value), therefore the fluid exits from outlet 61*b* crossing the always-open recycling conduit 60, is newly reintroduced into the separator, and thus contributes to increasing the fluid flow inletting into the separator. This is continued for as long as the fluid flow is not at the required level.

When the fluid flow circulating in the separator reaches the right pressure level for guaranteeing correct separation of the solid particles, which means a pressure on the obturator 62 equal to the first predetermined value, the obturator 62 is pushed towards its third position, in which the obturator 62 closes the outlet 61*b* of the valve 61.

In this operating condition the fluid enters the valve 61, cannot exit from the outlet 61*b* of the valve inasmuch as the valve 61 is closed by the obturator 62, and exits from the outlet 61*c* instead. At this point the pressure exerted by the fluid increases up to the second predetermined value, defined by the calibration of the elastic element 82, and causes the valve 63 to open, enabling the fluid to discharge through the outlet B of the separator.

The above-described separator operation thus allows the fluid to discharge only when the fluid flow rate is sufficient to guarantee effective solid particle separation. This is completely automatic and depends exclusively on the flow of the fluid through the separator.

Furthermore, the special construction of the functional elements of the separator, and in particular the valves 61 and 63, enables sure functioning of the separator and extreme simplicity of separator calibration. The calibration setting depends entirely on the weight and size of the float (obturator) of valve 61 and the calibration of the spring of valve 63. Also, the valves are made so as to be operable without dragging seals which would cause difficulties both of construction and of operation.

The separator can obviously be used with fluid inlet systems that are quite different from the one described; and valves 61 and 63 can be of different construction to what is described herein.

What is claimed is:

1. A cyclone separator suitable for variable fluid flow rates, for separating solid particles dispersed in a fluid, comprising a closed recipient superiorly closed by a lid provided with an inlet for the fluid including the solid particles and an outlet for the fluid purified of the solid particles, the recipient having a truncoconical wall converging in a downwards direction, at a narrow end of which there is a discharge which can be connected to a container in which the solid particles are collected, and above which an outlet conduit is located for outletting the fluid from the recipient; wherein it also comprises: a recycling conduit for placing the outlet conduit in communication with the inlet of the fluid; a three-way valve connected at an inlet thereof to the outlet conduit and connected at outlets thereof to the recycling conduit and to the outlet, which three-way valve is provided with an obturator commanded by a pressure exerted by the fluid exiting from the outlet conduit, which obturator blocks a connection between the outlet conduit and the recycling conduit when the pressure reaches a first predetermined value; a one-way valve having an obturator and being located on the outlet downstream of the three-way valve, which one-way valve is normally closed and is commanded by pressure exerted by the fluid outletting from the outlet conduit, which one-way valve connects the outlet conduit with the outlet when the pressure exerted by the fluid reaches a second predetermined value which second predetermined value is above the first predetermined value.

2. The separator of claim 1, wherein the obturator of the three-way valve and the obturator of the one-way valve are directly actuated by the fluid exiting the outlet conduit.

3. The separator of claim 2, wherein the lid comprises a second chamber, constituting the body of the one-way valve, internally of which the obturator of the one-way valve can slide and assume: a first position in which the obturator closes the one-way valve, which first position is maintained by a calibrated elastic element as long as a pressure of the fluid flow coming from the outlet conduit falls below the second predetermined value; a second position, in which the obturator opens the one-way valve, when the pressure of the fluid flow coming from the outlet conduit rises above the second predetermined value.

4. The separator of claim 3, wherein projecting guides are located on an internal wall of the second chamber, which projecting guides guide a sliding of the obturator without preventing passage of the fluid.

5. The separator of claim 1, wherein the lid comprises a first chamber constituting the body of the three-way valve, internally of which a calibrated float can slide in an axial direction, which float constitutes the obturator of the valve and which can assume: a first position, in which the obturator closes the inlet of the three-way valve, when there is no flow of fluid inletting from the outlet conduit; a plurality of second positions, in which the obturator opens both the inlet and the outlets of the three-way valve, when a flow of fluid arriving from the outlet conduit exerts on the obturator a pressure which is lower than the first predetermined pressure; a third position, in which the obturator opens the inlet and the outlet connected to the outlet of the three-way valve and closes the outlet of the three-way valve connected to the recycling conduit when the flow of fluid arriving from the outlet conduit exerts on the obturator a pressure which is superior to the first predetermined pressure.

6. The separator of claim 5, wherein the calibrated float constituting the obturator is a metal cylinder having two truncoconical ends.

7. The separator of claim 5, wherein the first chamber comprises: a channelled housing, directly connected to the inlet and the outlet of the three-way valve, internally of which the obturator of the three-way valve can slide without a seal; an annular chamber which is always connected with an inside of the channelled housing and with the outlet of the three-way valve.

* * * * *